(12) United States Patent
Culp et al.

(10) Patent No.: US 7,840,373 B2
(45) Date of Patent: Nov. 23, 2010

(54) SYSTEM AND METHOD FOR SELECTING A LOCATION FOR MARKING PLACEMENT

(75) Inventors: James C. Culp, Pleasanton, CA (US); Craig E. Farren, Livermore, CA (US); Artem Borovinskih, San Jose, CA (US); Eric Kuo, Foster City, CA (US)

(73) Assignee: Align Technology, Inc., Santa Jose, CA (US)

( * ) Notice: Subject to any disclaimer, the term of this patent is extended or adjusted under 35 U.S.C. 154(b) by 0 days.

(21) Appl. No.: 11/755,652

(22) Filed: May 30, 2007

(65) Prior Publication Data

US 2008/0300824 A1 Dec. 4, 2008

(51) Int. Cl.
*G01B 9/10* (2006.01)
(52) U.S. Cl. ............... 702/155; 702/156; 702/158; 702/166
(58) Field of Classification Search ............... 702/81, 702/117, 127, 152, 155, 167; 264/222, 155, 264/167; 345/419, 222; 433/24, 419
See application file for complete search history.

(56) References Cited

U.S. PATENT DOCUMENTS

| | | | | |
|---|---|---|---|---|
| 5,431,562 A | * | 7/1995 | Andreiko et al. | 433/24 |
| 5,857,853 A | * | 1/1999 | van Nifterick et al. | 433/213 |
| 6,165,406 A | * | 12/2000 | Jang et al. | 264/308 |
| 7,084,868 B2 | * | 8/2006 | Farag et al. | 345/419 |
| 7,293,988 B2 | * | 11/2007 | Wen | 433/24 |
| 7,352,891 B2 | * | 4/2008 | Suzuki et al. | 382/151 |

* cited by examiner

*Primary Examiner*—Hal D Wachsman
*Assistant Examiner*—Felix E Suarez
(74) *Attorney, Agent, or Firm*—Klein, O'Neill & Singh, LLP

(57) ABSTRACT

A system and associated method for selecting or creating an area which meets meet a set of marking criteria, for example, corresponding to a minimum surface area; a maximum slope angle; and a minimum deviation from a specified height. A marking station is directed to mark the selected area that meets the marking criteria.

27 Claims, 11 Drawing Sheets

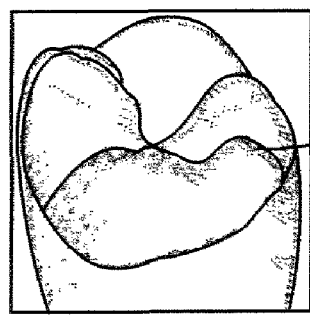
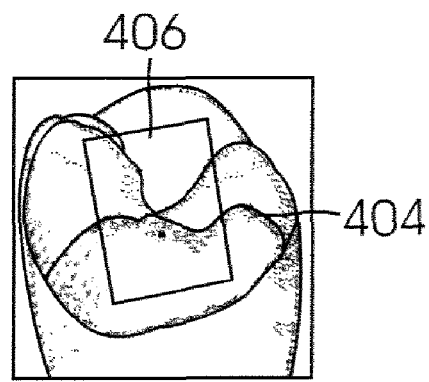
FIG. 4A
FIG. 4B
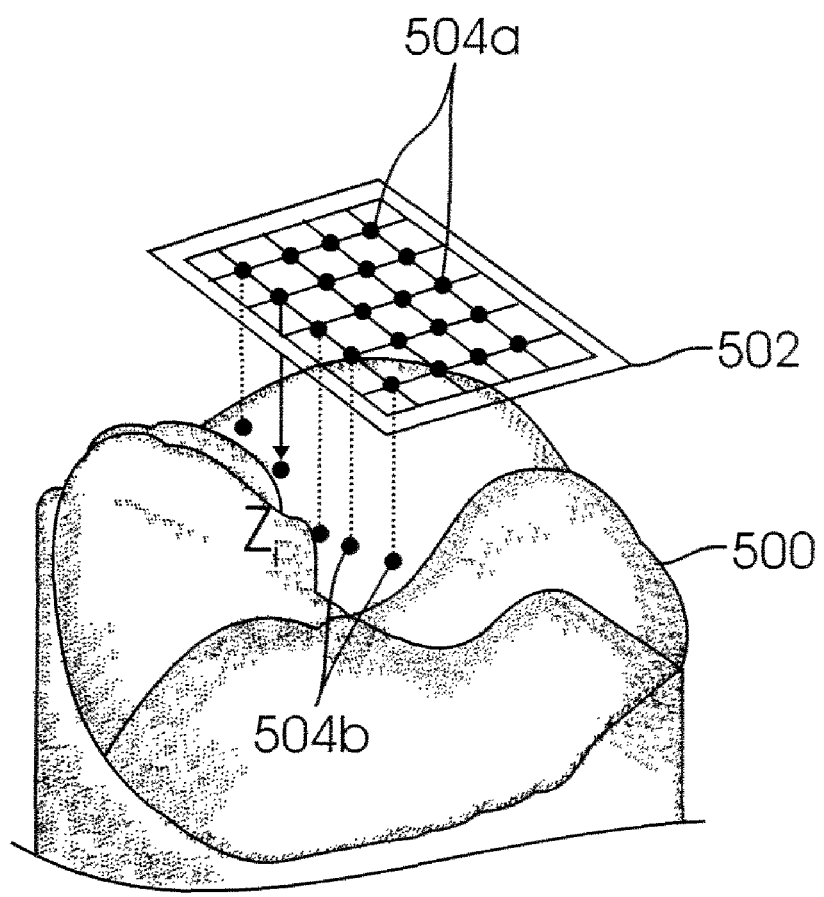
FIG. 5

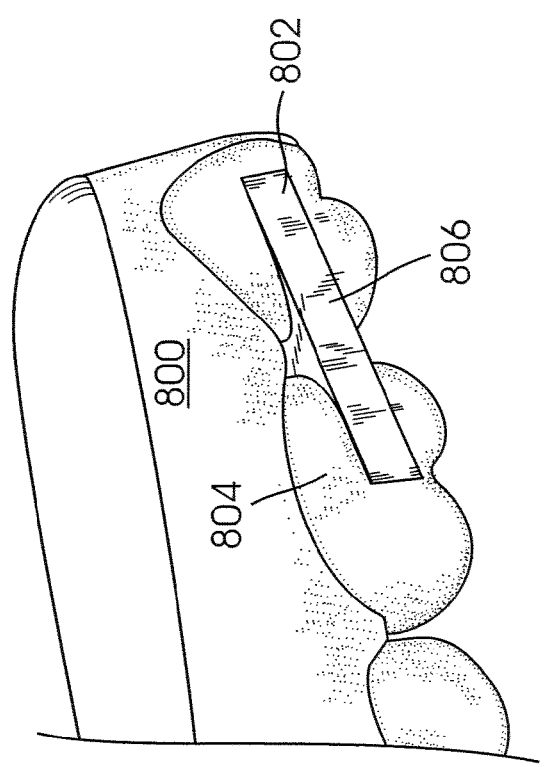
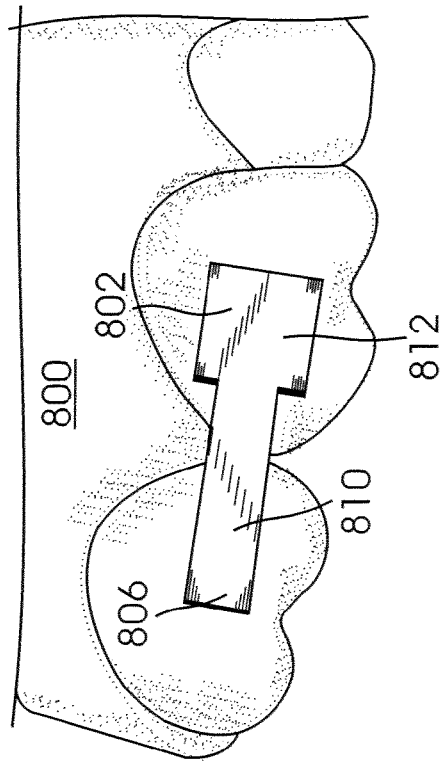

SYSTEM AND METHOD FOR SELECTING A LOCATION FOR MARKING PLACEMENT

BACKGROUND

1. Field of the Invention

This invention relates to the marking of objects, and more particularly to a system and associated method for selecting a location for marking placement.

2. Related Art

It has become common practice to mark products with labels, identification numbers, and company logos. For example, laser marking (LM) can provide a permanent marking with high contrast that does not wear off or degrade with use. Traditional marking systems however, may have limited marking range and can only be used effectively to provide marking on relatively large areas and flat surfaces.

Unfortunately, many surfaces that may require marking are relatively small and uneven. This is especially true in the medical prosthetics industry, where marking quality may be adversely affected by extreme anatomy. For example, in the dental appliance manufacturing industry, the marking quality on dental aligners may be adversely affected by abnormal dental structures, such as, steeply-tilted molars, or molars having sharply-sloping occlusal surfaces.

Since the dental aligner contour is unique for each dental aligner, printing or placing stickers or embedded identifier tags within the dental aligner material is subject to distortion. Corrections to the aberrations are challenging in the absence of complex mathematical formulas applied to the image to be printed.

What is needed therefore is a system and associated method for locating or creating a location on an object, which may have a limited marking area and/or an uneven surface suitable for marking.

SUMMARY

The present invention provides a system and associated method for selecting or creating a location and position for a mark to be placed on an object, which may have a limited marking area, an uneven surface or both.

In one aspect of the present invention, a method and system is provided for locating a marking position on one or more selected areas of an item. This aspect includes determining that one or more selected areas of an item has at least a minimum surface area; determining a plurality of height measurements relative to a reference level and locations on each of the one or more selected areas; determining the average of the measured heights for each of the one or more selected areas; calculating the absolute value of the height difference between the average of the measured heights and an optimum height to generate an absolute height value for each of the one or more selected areas; determining a slope value for each of the one or more selected areas; and selecting a marking area from the one or more selected areas for marking having at least the smallest slope value and the smallest absolute height.

In another aspect of the present invention, a method is provided for creating a marking position on one or more selected areas of an item. The method includes generating a first data set representing a first configuration; generating a second data set representing an area offset relative to the first configuration; and forming a mold using the first data set and the second data set.

A more complete understanding of the invention can be obtained by reference to the following detailed description of the embodiments thereof in connection with the attached drawings.

BRIEF DESCRIPTION OF THE DRAWINGS

The above and other objects, features and advantages of the present invention will become more apparent from the following detailed description when taken in conjunction with the accompanying drawings in which:

FIGS. 4A and 4B are simplified illustrations of a crown projection and a bounding rectangle, respectively in accordance with an embodiment of the present invention;

FIG. 5 is a simplified illustration of a model for determining molar height and slope in accordance with an embodiment of the present invention;

FIGS. 8A and 8B are simplified illustrations of a dental mold including an offset area in accordance with an embodiment of the present invention.

DETAILED DESCRIPTION

Figure 1:
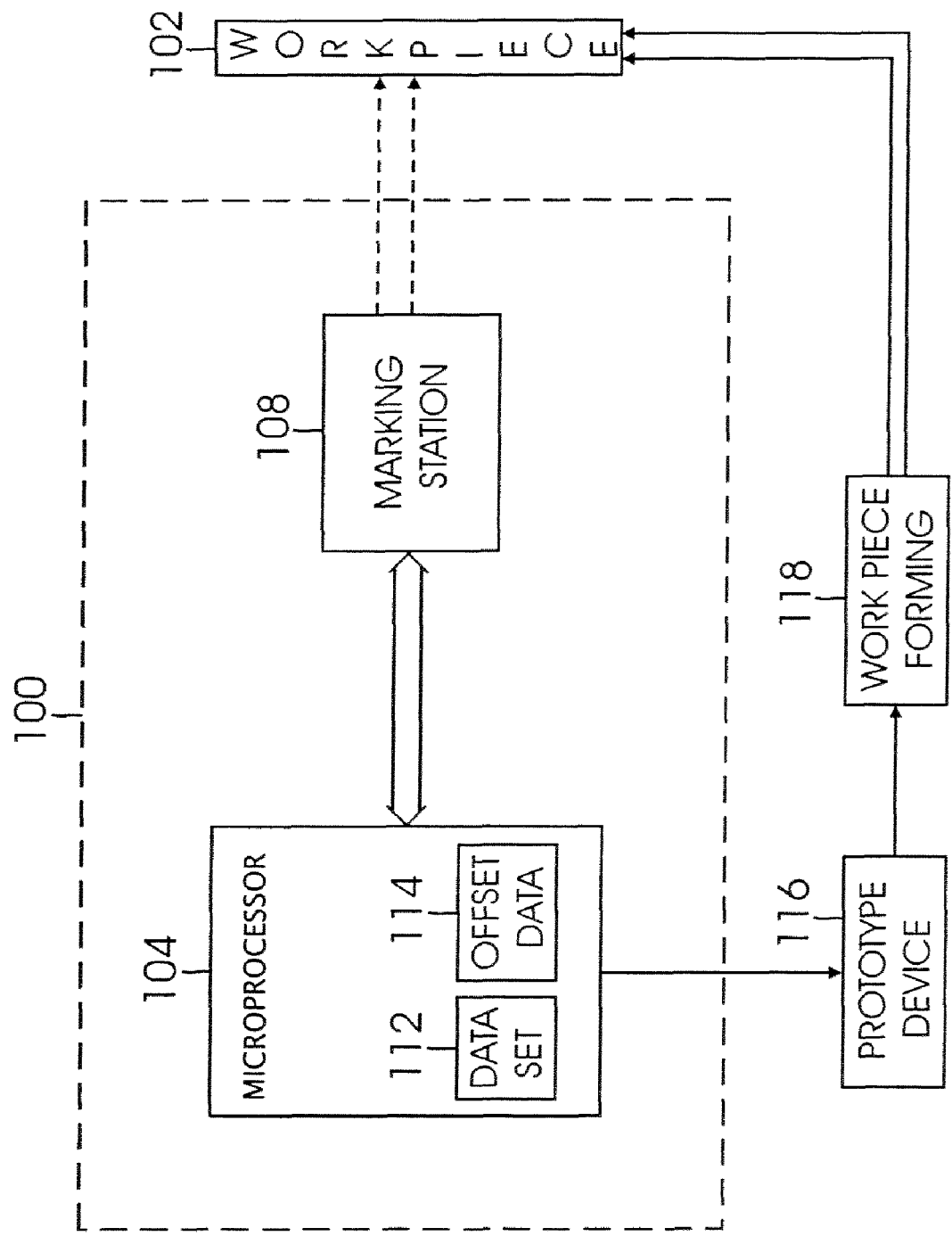
FIG. 1 is a block diagram of a marking system in accordance with an embodiment of the present invention.

In the detailed description of the invention that follows the invention is described primarily in the context of a system and associated method for locating, selecting and creating an area suitable for marking on an object, such as on mass produced, customized dental appliances. It should be understood however, that the system and method of the present invention may be employed in the locating, selecting and creating of an area suitable for marking on any of various types of workpieces, having limited marking area and uneven marking surfaces, such as, prosthetic body parts, athletic gear, implantable hearing aids and the like.

Furthermore, although a marking device described herein in connection with the embodiments of the invention is a laser, it will be apparent that other types of marking devices known in the art, such as ink jet printers, ultrasonic devices, CNC machines, and the like, may be employed in place of, or in conjunction with, the laser. In addition, any number of tinted, invisible (identifiable with a light source) or fluorescent inks may be used to enhance the visibility of the marks.

The system and method of the present invention are well adapted for use in marking items with uneven marking surfaces, such as dental appliances, particularly dental aligners. In such an application, the present invention advantageously includes determining which of the tooth areas meet a set of marking criteria corresponding to, for example, a minimum occlusal surface area; a maximum slope angle; and a minimum deviation from a specified height. The marking station is directed to mark a selected tooth area that meets the marking criteria.

In one embodiment, if the selected area is determined to correspond to a rearmost molar, the marking station maybe directed to shift the marking slightly forward to compensate for possible trimming at rearmost edges of the aligner.

The system may optionally direct the marking station to mark the tooth area that best meets the marking criteria with a first marking (such as an identification number), and to mark the tooth area that next best meets the criteria with a second marking (such as a logo, trademark, or trade name). The marking may be accomplished with a laser or equivalent marking apparatus.

The system and method of the present invention are also well adapted to create a uniform flat raised surface on one or more portions of the dental aligner to enable labeling or otherwise identifying the dental aligner with marking, such as laser marking, ink jet, laser jet, stickers (including adhesive compliance indicators and branding) and/or other print or decorative graphics in a non-distorted and automated fashion.

In this embodiment, a shape is created of uniform contour and positioned on a mold, such that the shape is subsequently built into the dental aligner so that an identification tag or graphic can be added to, etched on, or built into the dental aligner without distortion to the dental aligner. In this embodiment, the shape can be located or positioned anywhere on the dental aligner, for example, the shape may be placed on a posterior buccal surface or an upper lingual area.

FIG. 1 is a block diagram representing a marking system 100 in accordance with an embodiment of the present invention. Marking system 100 includes a microprocessor 104 and a marking station 108 for locating and selecting an area on workpiece 102 suitable for marking.

In an exemplary embodiment, workpiece 102 is a dental "aligner", which is formed from a mold made from an impression of a patient's teeth.

Producing dental molds, for example, with a rapid prototyping device 116 or the equivalent, requires the use of a computerized model or digital data set representing the dental geometry and tooth configuration. The computerized model of the patient's teeth may be manipulated to portray a new tooth arrangement (i.e. an orthodontic prescription) and subsequent molds may be produced to reflect each successive arrangement in the prescription. This may be repeated any number of times to derive a number of molds with differing tooth arrangements.

Figure 2:
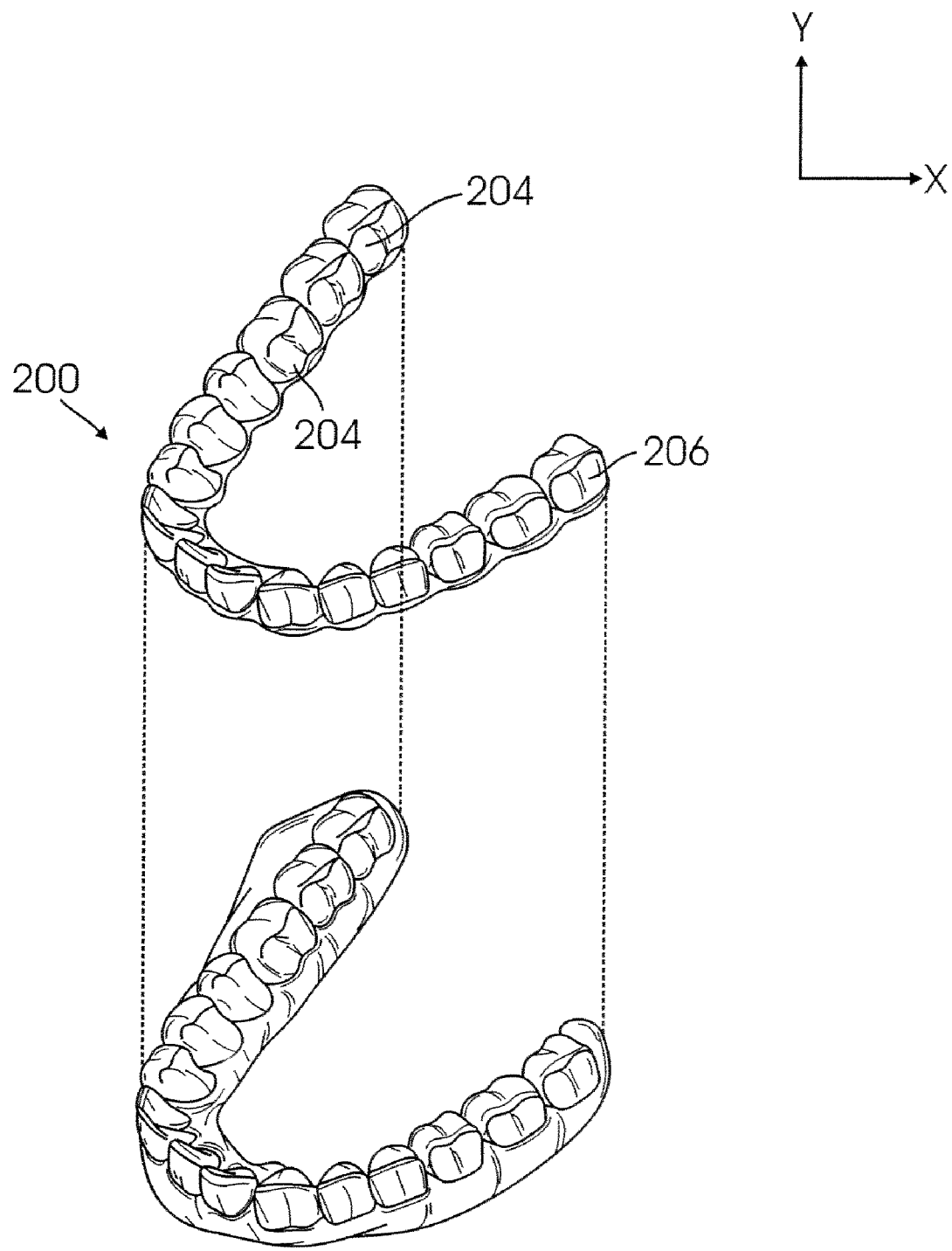
FIG. 2 is a simplified illustration of a dental aligner in accordance with an embodiment of the present invention.

In the present invention, the series of computer models or digital data sets 112 (hereafter "data sets 112") representing the dental geometries or orthodontic prescription associated with each of the series of molds, is generated and stored on microprocessor 104. For reasons described in more detail below, microprocessor 104 may also include offset area geometry data 114. Subsequently, the series of molds made from rapid prototyping device 116 are used to fabricate a series of representative workpieces 102. As shown in FIG. 2, a series of dental aligners 200 having an inner surface 204 and an outer surface 206 may be created by disposing molds in, for example, a thermoplastic fabrication machine 118.

As also shown in FIG. 2, dental aligner 200 can be physically associated with an identifier (not shown) that provides patient ID and other identifying characters that associate a specific aligner 200 to a patient. In one embodiment, the identifier may be a barcode, RFID, microchip or similar identification means. In operation, identification data is extracted from the identifier to provide the patient ID information to microprocessor 104 to match geometric data sets 112, as described below, with a particular aligner 200 during the manufacturing process.

Figure 3A:
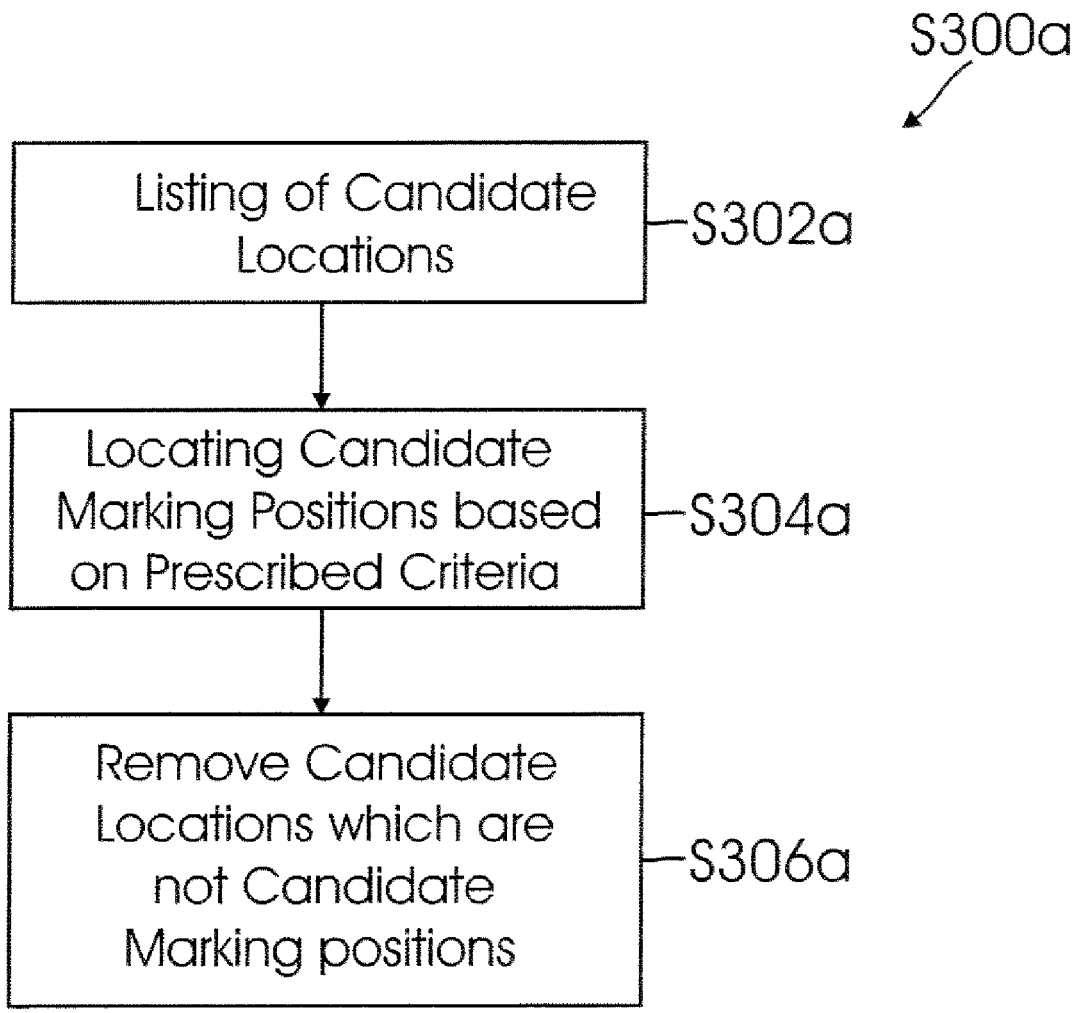
FIG. 3A is a flowchart illustrating the mark location selection process in accordance with an embodiment of the present invention.

FIG. 3A shows a flowchart representing a system 300a to locate or select the marking location based on geometric data in accordance with an embodiment of the present invention. As shown in FIG. 3A, in step s302a, a list of candidate locations for marking is generated using predetermined selection criteria. The selection criteria may include such choices as, location, surface texture, impediments and the like of any tooth.

In step s304a, for each candidate location the geometrical characteristics of the location are determined. In one embodiment, the surface area of each candidate location is calculated from data set 112, which includes data representing the configuration and geometric attributes of the candidate location, to determine if enough area is present to apply the mark. In one embodiment, the surface area is checked by projecting the surface area to the xy-plane to create a projection and verifying that the mark's bounding rectangle lies entirely inside the projection. Moreover, the height and slope of the molar surface is calculated as described in detail below.

In step s306a, candidate locations that do not meet the minimum surface area requirement, the height threshold or the desired slope value are removed from the list of candidate locations.

Figure 3B:
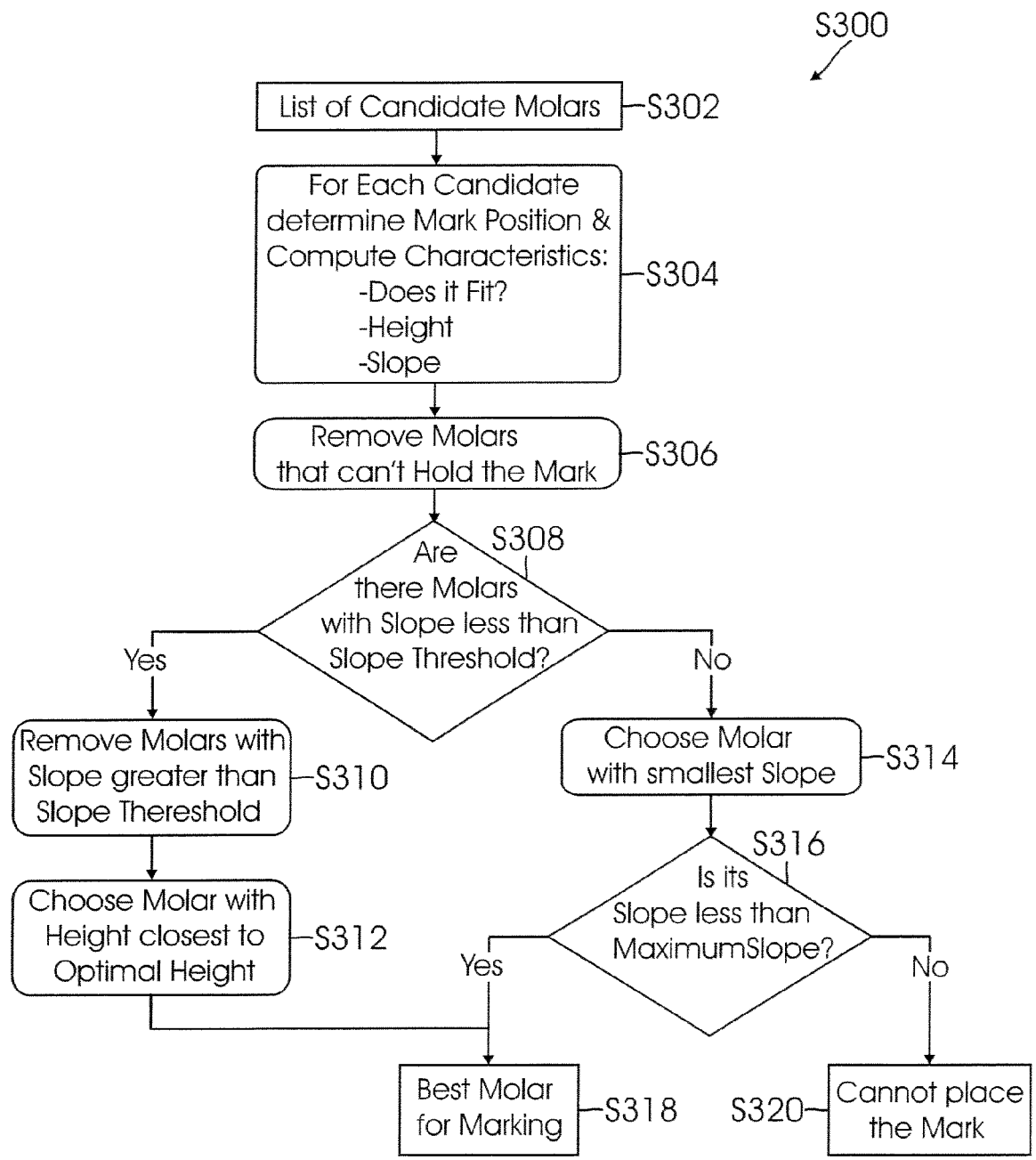
FIG. 3B is a flowchart illustrating the mark location selection process in accordance with an embodiment of the present invention

In one exemplary embodiment, microprocessor 104 performs data analysis functions using data sets 112 to locate or select the marking location based on geometric data in accordance with the process s300 set forth in FIG. 3B.

As shown in FIG. 3B, in step s302 using the prescription data found in data sets 112, a list of candidate locations is generated. In one embodiment, the list of candidate locations includes all molar teeth, with the exception of back molars, which may include wisdom teeth. Optionally, if it is subsequently determined that molars on the candidate list do not provide an adequate marking location then back molars may be considered.

In step s304, for each candidate location the geometrical characteristics of the location are determined. In one embodiment, the surface area of each candidate molar's crown is calculated from the data in data sets 112 to determine if enough area is present to apply the mark. In one embodiment, the surface area is checked by projecting the crown to the xy-plane to create projection 404 (FIG. 4A) and verifying that the mark's bounding rectangle 406 (FIG. 4B) lies entirely inside projection 404. Optionally, when fitting the mark to back molars, the bounding rectangle may be extended by a predefined value to prevent cutting the mark in subsequent trimming operations.

As shown in FIG. 5, to determine the height and slope of the molar, as shown in FIG. 5, crown 500 is sampled with a regular grid of points 502. Each point 504a is then projected on the crown's surface as points 504b. The z-axis coordinates of projections Zi are collected and stored in data sets 112. The average height of the molar is defined as the mean value of Z, and the slope is defined as the dispersion of the projected points 504b.

Referring again to FIG. 3B, in step s306, locations that do not meet the minimum or threshold requirements of fit, height and slope are eliminated as candidates.

In step s308, the slope of the remaining candidate marking location is compared to a slope threshold defined below. In one embodiment, if molars exist with slopes less than the slope threshold, then molars with a slope greater than the slope threshold are removed from the list of candidate locations (s310). Next, a molar is chosen with a height closest to the optimal height defined below (s312), which becomes the selected molar for marking (s318).

In the event that there are no molars with a slope less than the slope threshold, a molar is chosen with the smallest slope of each candidate (s314). This slope is then compared to a maximum slope value (s316). If the molar has a slope less than the maximum slope value then the molar is selected for marking (s318). If the slope value is higher than the maximum slope then the mark cannot be placed (s320).

During the marking process, marking station 108 directs a marking head or the equivalent to the target marking location. The marking head marks selected areas of aligner 200 with information received from microprocessor 104.

Figure 6A:
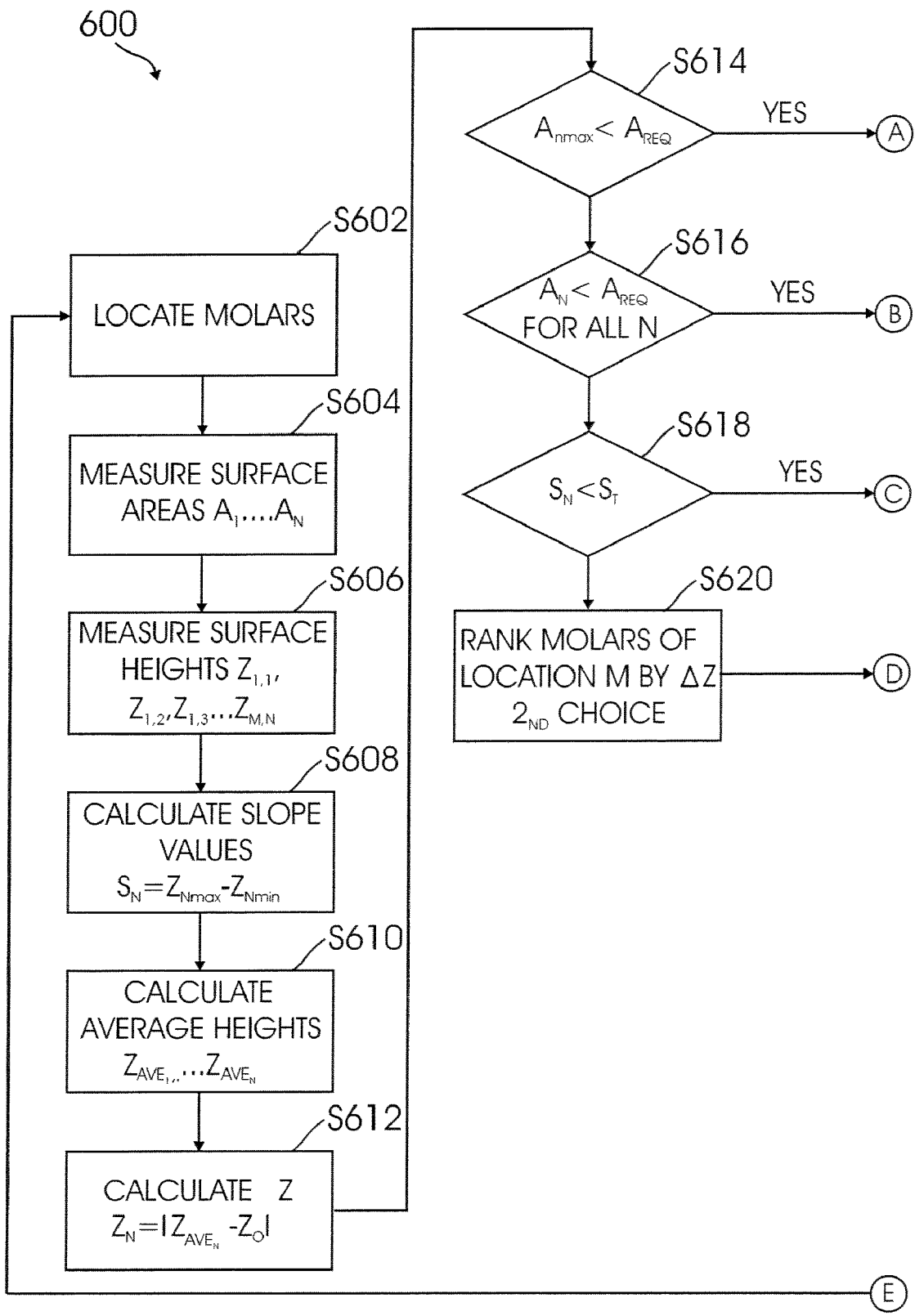
FIGS. 6A and 6B are flowcharts illustrating a method for locating and selecting a marking area in accordance with an embodiment of the present invention.
Figure 6B:
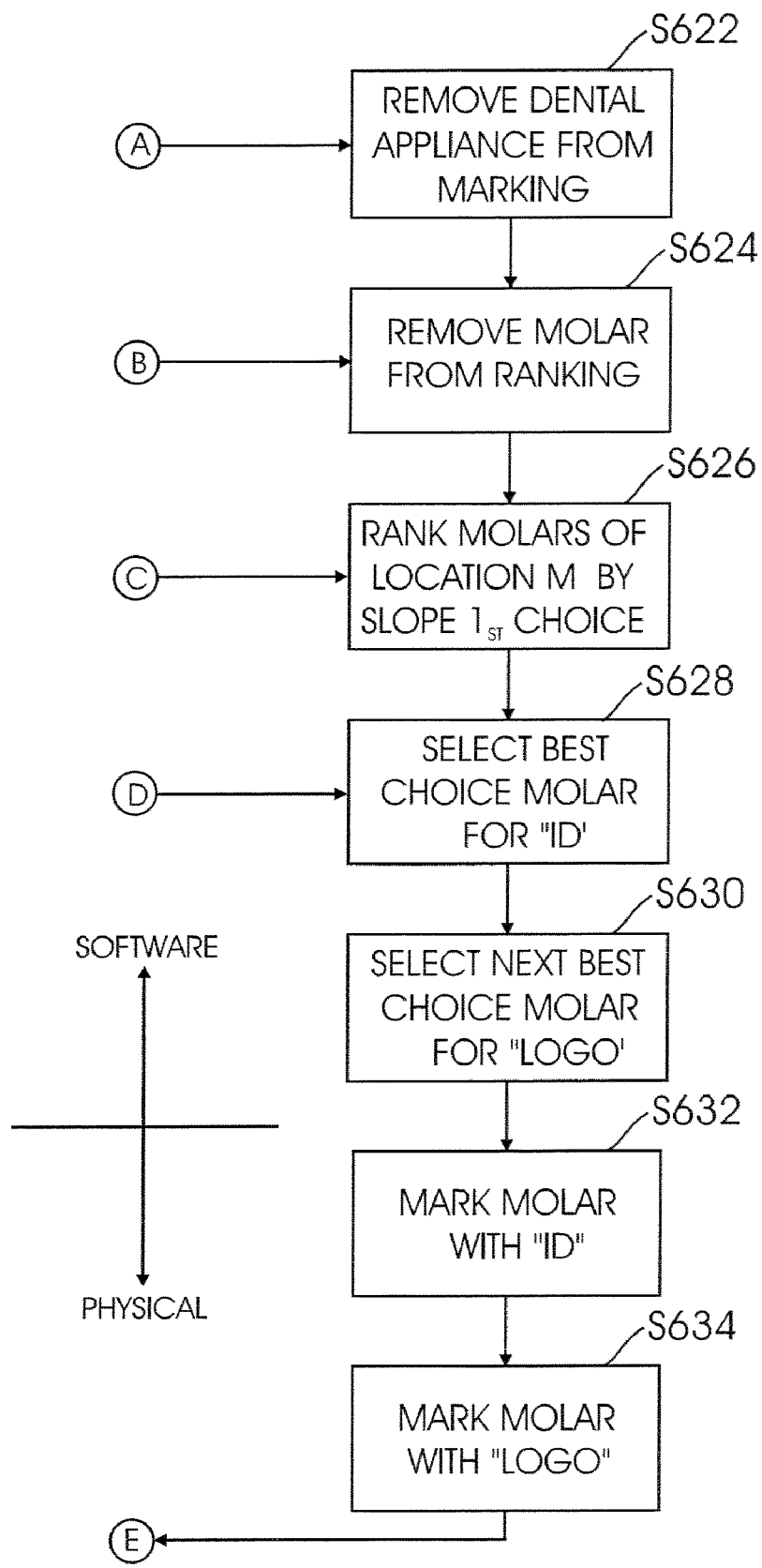

FIGS. 6A and 6B provide a flow chart illustrating a method 600 for selecting and locating a marking location on the surface of an object, such as on aligner 200 (FIG. 2) in accordance with the present invention.

In steps s602 and s604, geometric data from data sets 112 (FIG. 1) are processed to locate candidate molars and measure tooth surface areas. Of these tooth areas, those that correspond to the occlusal surface areas of molars are located, and, optionally, those that correspond to the rearmost molars are identified. For example, each tooth area may be assigned a number from 1-16 for a full dentition set in an upper or lower jaw, with the number sequence beginning with "1" for the rearmost molar on one side, and ending with "16" for the rearmost molar on the opposite side. For a dentition set lacking third molars ("wisdom teeth"), the sequence would be 1-14. Thus, the tooth areas 1 and 16 for a full dentition set (1 and 14 for a set lacking third molars) are identified, and may be designated for "forward-shifted" marking (described below) due to concerns over post-marking trimming processes, if at least one of these areas is selected for marking based on the minimal slope and optimal height criteria discussed below. As will be discussed below, the size, slope and deviation from an optimum height for the occlusal molar surfaces are important factors determining the quality of laser marking.

In step s606, a plurality of height measurements, relative to a reference level $Z_R$, are performed at each occlusal surface area to obtain accurate height values $(Z_{1,1}, Z_{1,2}, Z_{1,3}, \ldots Z_{M,N})$, where M represents the number of measurement per surface area, while N represents the number of surface areas.

In step s608, the slope value $S_N$ is calculated for each occlusal surface area by Equation (2):

$$S_N = Z_{Nmax} - Z_{Nmin} \quad (2)$$

where $Z_{Nmax}$ and $Z_{Nmin}$ are the maximum and minimum measured height values associated with surface N respectively.

In step s610, the average height $Z_{AVE_N}$ of an occlusal surface N is calculated by Equation (3):

$$Z_{AVE_N} = (Z_{N,1}, Z_{N,2}, Z_{N,3}, \ldots Z_{N,M})/M \quad (3)$$

In step s612, the absolute value of the deviation or difference $\Delta Z_N$ from a predefined optimum height value $Z_O$ is calculated by Equation (4):

$$\Delta Z_N = |Z_{AVE_N} - Z_O| \quad (4)$$

where $Z_O$ is the optimum height of an occlusal surface area. The value of $Z_O$ for dental appliances such as aligners may be, for example, 12 mm.

In step s614, it is determined whether a particular dental appliance is suitable for marking. The dental appliance needs to have at least one occlusal surface area that is equal to or larger than a predetermined minimum required surface area $A_{REQ}$. For the marking of an identification number on a dental appliance such as dental aligner 200 (FIG. 2), the minimum required area $A_{REQ}$ may be about 28 mm² (4 mm in depth by 7 mm in width). This area is sufficient for the marking of first and second parallel rows of up to 6 alphanumeric characters per row, where each character is 1.2 mm in depth (as measured along the X-axis in FIG. 2) by 0.9 mm in width (as measured along the Y-axis on FIG. 2). If aligner 200 does not have an occlusal molar surface with the required minimum surface area, it is removed from marking in step s622, or it may be segregated for marking by alternative means or with a different marking indicia. If the only area meeting this criterion is an area corresponding to a rearmost molar, the appliance is designated for "forward-shifted" marking, where the marker is directed to shift the marking area slightly forward (i.e., along the Y-axis in FIG. 2) to compensate for trimming at the rear edges of the aligner.

In step s616, it is determined which particular tooth areas of an appliance corresponding to molars do not have the minimum occlusal surface area. Tooth areas lacking the required area are removed from a list of possible marking sites in step s624.

In step s618, it is determined which particular occlusal molar surfaces have slopes that are less than a predetermined threshold value $S_T$. Surfaces having slopes less than the threshold value are then ranked or prioritized by slope, as represented in step s626, with the highest ranking being given to the occlusal molar surface having the smallest slope. Surfaces having slopes greater than or equal to the threshold slope value are ranked or prioritized by deviation ($\Delta Z$) from the optimum height, as represented by step s620, with the highest ranking being given to the occlusal molar surface having the smallest $\Delta Z$. In one embodiment, the slope is defined as the dispersion of the projected points 504b as shown in FIG. 5.

In step s628, the molar surface ranked highest by either of the ranking steps s620 or s626 is selected for marking with primary indicia (e.g., a unique identification number). In step s630, the next highest ranking molar surface is selected for marking with a secondary indicia (e.g., a logo, trademark, or trade name). The marking of the selected molar surface(s) with the primary (and optional secondary) indicia is performed in steps s632 and s634. As mentioned above, if a rearmost molar surface is selected for marking, a "forward shift" command is directed to marking station, whereby the marker is directed to shift the marking area on the selected surface slightly forward (along the Y-axis in FIG. 2) to allow for trimming of the rearmost edges of aligner 200 without compromising or impinging on the marking.

Figure 7A:
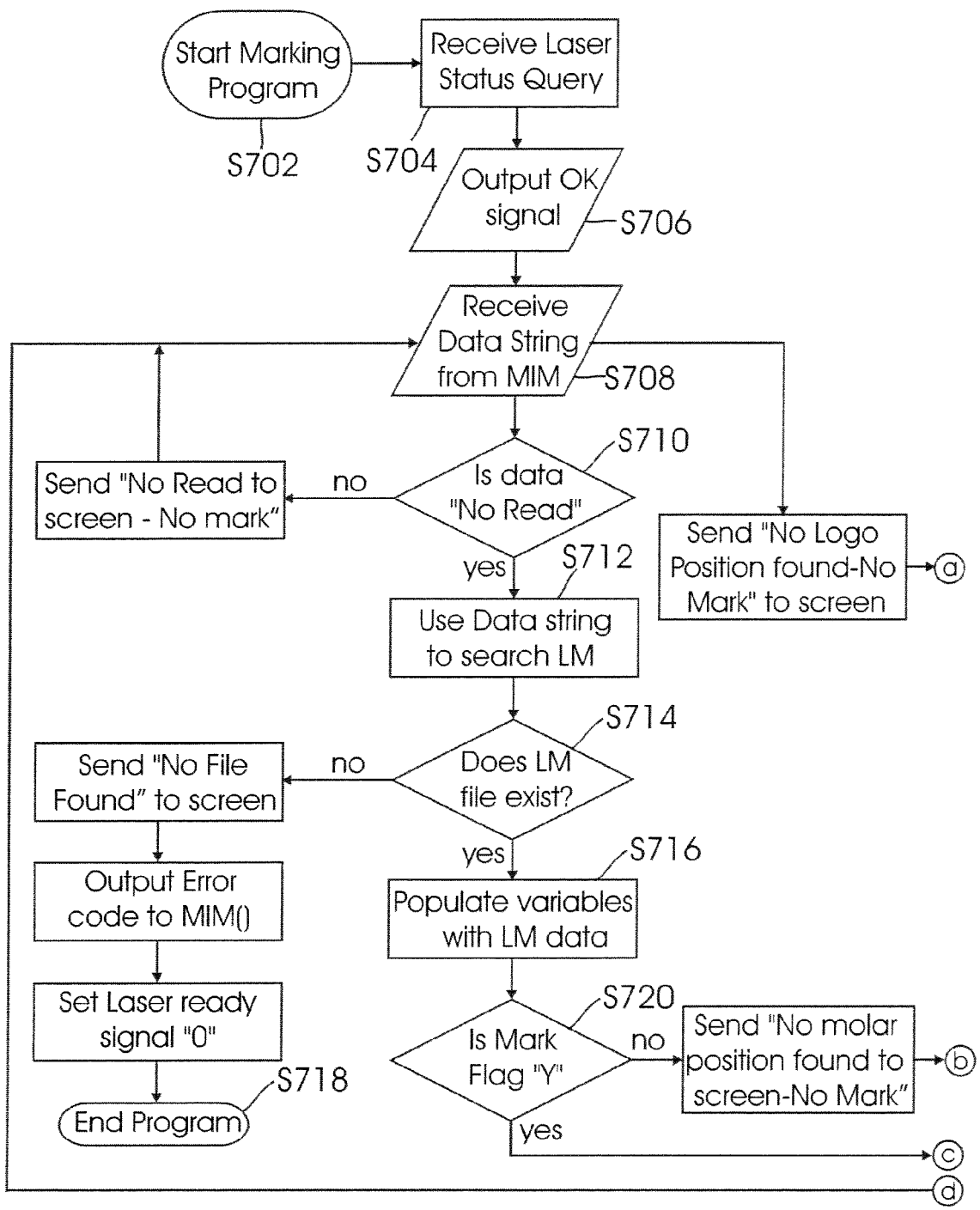
FIGS. 7A and 7B are flowcharts illustrating a method for operating a laser marking station in accordance an embodiment of the present invention.
Figure 7B:
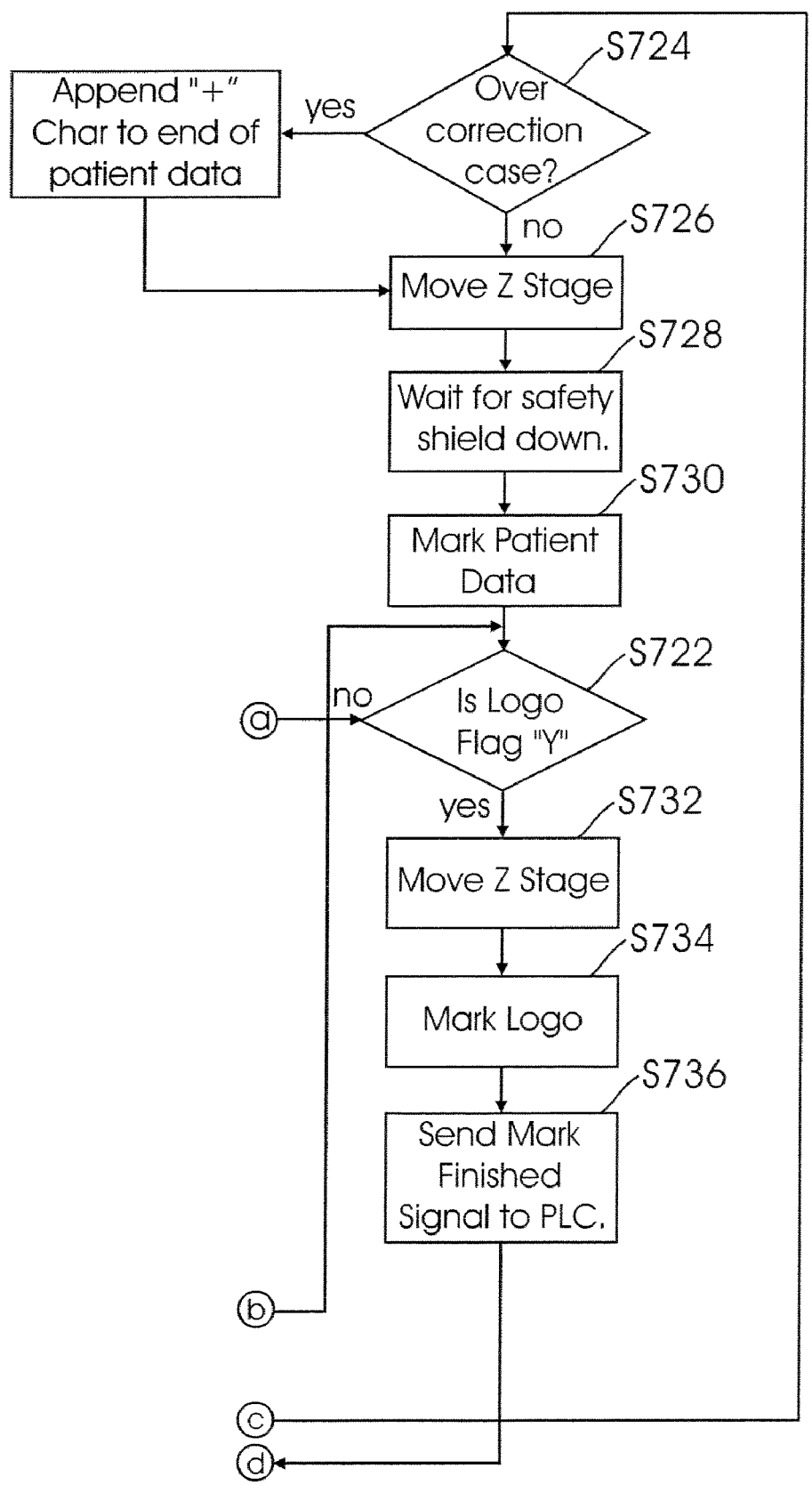

FIGS. 7A and 7B show a flow chart or process diagram illustrating the steps of a method for operating marking station 108 (FIG. 1) in accordance with the present invention. Marking station 108 is controlled by microprocessor 104, which, in one embodiment, includes a programmable logic controller (PLC, not shown), that manages the electrical and pneumatic functions of marking station 108. The PLC can store and retrieve multiple data sets 112, as well as the operational software that controls the system. In the following description, only basic operations that are necessary to understand the flow of the marking process are described.

In step s702, a command is received to start the marking operation. In this embodiment, marking station 108 is a laser marking station 108. This is followed by step s704, in which the system receives a laser status inquiry, and, in response, outputs a "READY" or "OK" signal (step s706), indicating that the system is ready to begin the process.

In steps s708 and s710 it is determined what data are to be used for marking. In steps s712, s714 and s716, it is determined that if the required marking data exist, the data are loaded into the marking station. If not, the marking process terminates at step s718.

In steps s720 and s722, it is determined whether a primary (ID number) or a secondary (logo, trademark, trade name) marking is to be performed. In case of a primary marking it is determined at step s724 if any additional information needs to be added. If it is needed, the data field is appended.

In steps s726, s728 and s730, the laser marking head is directed to a first predetermined marking area and imprints the primary marking indicia at the first marking area. In steps s732, s734, and s736, the laser marking head is directed to a second predetermined marking area and imprints the secondary marking indicia at the second marking area. After the markings are completed in step s736, the process returns to step s708 to receive the next marking request.

In some instances, the above identified analysis may not yield a suitable option for selecting and locating a marking location on the surface of an object. Alternatively, the system and method may be used to complete a similar analysis with the process described in FIG. 7, in conjunction with a prescription from a doctor, to determine the best location for a platform to be made to accommodate a label or laser marking on the side of the teeth positioned on the in or outside of the aligner.

FIGS. 8A and 8B are simplified representations of a dental mold 800 including an offset area or shape 802 in accordance with an embodiment of the present invention. Offset area 802 defines a flat raised portion 806 of aligner 200 (FIG. 2) through the modification of mold 800 used to create aligner 200, to enable the addition of non-distorted text, graphics, and or any other identification.

In one embodiment, mold 800 is formed, as previously described, employing a rapid prototyping device 116, such as a stereolithography machine, a fused deposition modeling machine or the equivalent. Rapid prototyping machine 116 selectively hardens a liquid or other non-hardened resin into a three-dimensional structure, which can be separated from the remaining non-hardened resin, washed, and used as a mold for producing aligner 200. Prototyping machine 116 receives the individual digital data sets 112 (FIG. 1) and produces one structure corresponding to each of the desired aligners 200.

In accordance with the present invention, digital data sets 112, including the mold geometry data, may be augmented with offset area geometry data 114 (FIG. 1). The offset area geometry data 114 represents the size, shape and position of offset area 802 relative to the mold geometry data in data sets 112. The offset area geometry data 114 may be added either virtually or actually to create offset area 802 on an anterior surface (not shown) or posterior surface 804 of aligner 200.

Subsequently, the offset area geometry data 114 may be used to guide the automated placement of an identification label/tag which may be placed on top of flat surface 806. Flat surface 806 may be placed in a unique position on each aligner 200 and, thus, automation of placement of an identification device is accomplished knowing the coordinates of flat surface 806. For example, because the location of flat surface 806 is known relative to the geometry of aligner 200, marking station 108 can direct a laser, printer, labeler or an equivalent marking mechanism to flat surface 806.

In one embodiment, the position of offset area 802 may be automatically predetermined by tooth number(s) which may be pre-fixed or user-determined. Also, the location on each tooth may be a pre-fixed location and orientation (e.g. center of the tooth, parallel to the horizontal plane) or vary depending on the tooth number(s) selected (e.g. facial center of the tooth for teeth Nos. 4-13, middle of mesiofacial cusp for teeth Nos. 1-3 and 14-16).

In another embodiment, the position of offset area 802 may also be determined by dental contour. For example, the flattest portion of the tooth may be calculated from data set 112 and selected as the location for placement. Alternatively, a user may manually select the location for placement of offset area 802 during the preparation of data set 112. A representation of offset area 802 may be positioned or painted onto the surface by the user for visual inspection and adjustment as needed.

In yet another alternative embodiment, offset area 802 may be created apart from mold 800 or aligner 200 as a "separate" platform. The separate platform may be formed using the shaping and locating data and techniques described with other embodiments, but may be adhered to aligner 200 using an adhesive. The marking of the separate platform could occur when the separate platform is being manufactured.

In yet another embodiment, aligner 200 with offset area 802 may be formed using a photolithographic apparatus or PLA. In this embodiment, there is no positive or mold for aligner 200 to be formed over. The design of aligner 200 with offset area 802 may be created using the same shaping and locating data and techniques described with other embodiments. However, in this embodiment aligner 200 with offset area 802 is formed directly as a 3-dimensional solid using photosensitive material.

FIG. 8B shows an alternative embodiment of offset area 802, which includes a narrow portion 810, for such identification devices as a logo, and a wider portion 812 to the side of narrow portion 810, for such devices as a compliance indicator. It should be understood, however, that offset area 802 can be formed into any appropriately suitable shape, size and position on aligner 200 to account for variable logo and font sizes.

The marking on flat surface 806 may also be performed on the inner surface 204 of aligner 200 as opposed to the outer surface 206 (FIG. 2). Offset area 802 positioned on the anterior surface of mold 800 may accommodate inner labeling with physical labels, since offset area 802 positioned on the anterior surface allows for placing labels without interference to the adaptation of aligner 200 to the patient's teeth. Inner surface 204 placement also provides the benefit of reduced exposure to the oral environment. In one embodiment, for placement on inner surface 204, the marking may be mirror-inverted such that when viewed through the transparent or translucent aligner 200, it appears in the proper orientation. Offset area 802 placed on the anterior surface may also accommodate electronic tags such as RFID labels which may have a thicker prominence than decal or thin-film sticker-type tags.

In addition, offset area 802, or any area deemed suitable for marking according to all embodiments of the present invention, may be marked with tinted, fluorescent or light sensitive ("invisible") inks or have a tinted, fluorescent or light sensitive ink added thereon. The light sensitive inks may respond to, for example, sunlight, red, blue or "black" light, such that the mark becomes visible only under certain lighting conditions. The mark may also be made to "glow" in the absence of light.

In one embodiment, the mark may be etched or drawn on offset area 802 using creative artistic presentation techniques well known in the art, which allow the mark to appear 3-dimensional. Alternatively, artistic presentation techniques, such as varying outline thicknesses, grooving, or mounding, may also be used to make the mark appear visible only from specific angles relative to the patient wearing the marked product.

In one embodiment, a non-toxic label or decal may be applied using a non-toxic adhesive to flat surface 806 of offset area 802 formed on aligner 200 created from mold 800, manufactured as a separate platform or formed using a photolithographic system.

Figure 9:
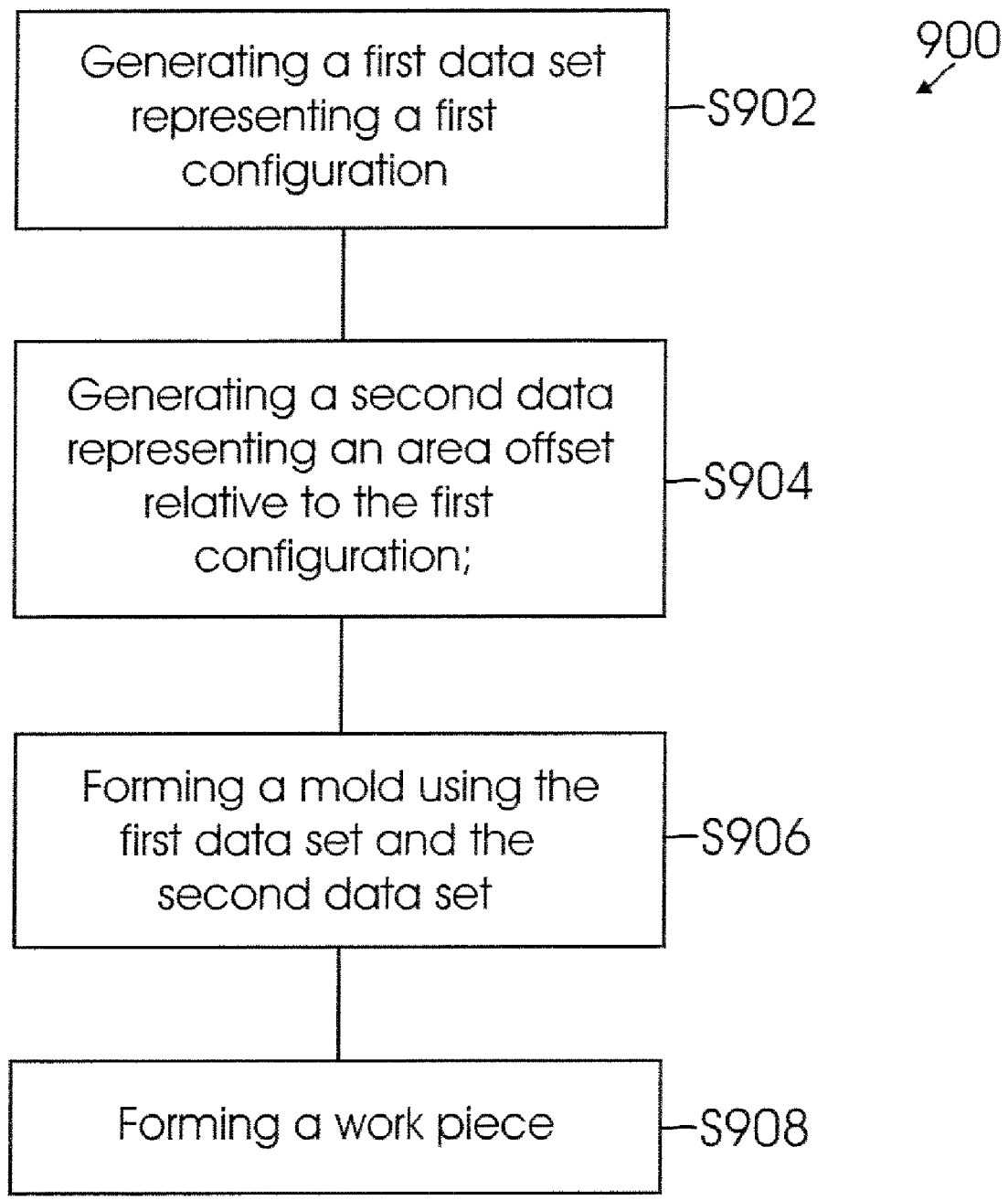
FIG. 9 is a flowchart illustrating a method for creating a marking area in accordance with an embodiment of the present invention.

FIG. 9 is a flowchart illustrating the steps of creating offset area 802 on the inner or outer surface of mold 800. In step s902, data set 112 is generated, as described above, and includes data representing a first configuration, such as a dental configuration and tooth geometry.

In step s904, data set 112 is generated and includes offset area geometry data 114, which represents the size, shape and position of offset area 802 relative to the data in data set 112. Offset area geometry data 114 may be added either virtually or actually to create offset area 802 on a posterior surface 804 of aligner 200.

In step s906, data set 112 and offset area geometry data 114 are used in conjunction or are combined to create a single mold structure, which includes offset area 802 positioned in the desired location.

Mold 800 having offset area 802 can then be used with, for example, thermoplastic fabrication machine 118 to create aligner 200 having an offset area 802 defining flat surface 806. Marking station 108 can direct a laser, printer, labeler or an equivalent marking mechanism to flat surface 806 for placing an information device on flat surface 806.

While the present invention has been shown and described with reference to specific embodiments thereof, it will be understood by those skilled in the art that various changes in form and details may be made therein without departing from the spirit and scope of the invention.

What is claimed is:

1. A computer implemented method for locating and selecting a marking position on an item, the method comprising:
   selecting using a processor one or more surface areas from a representation of a plurality of tooth crowns that meet a set of marking criteria corresponding to a minimum surface area;
   measuring using a processor the absolute height and slope value of discrete locations on each of the one or more selected surface areas; and
   selecting a marking area that corresponds to a location on an item that is positionable on the tooth crowns and that corresponds to one of the one or more selected surface areas having an absolute height and slope value that meets a threshold.

2. The method of claim 1, further comprising marking the marking area using a laser.

3. The method of claim 1, further comprising marking the marking area using an ink printing device.

4. The method of claim 1, wherein the item comprises a prosthetic device.

5. The method of claim 1, wherein the one or more selected areas each comprise a substantially uneven surface.

6. The method of claim 1, wherein the marking area comprises a platform formed on a space corresponding to an area between two of the one or more selected surface areas.

7. The method of claim 1, wherein the item comprises a dental aligner.

8. A computer implemented method for locating a marking position on one or more selected areas of an item, the method comprising:
   selecting using a processor one or more surface areas from a representation of a plurality of tooth crowns, the one or more surface areas when projected to a plane each create a projection having at least a predetermined minimal area inside the projection;
   determining using the processor a plurality of height measurements made relative to a reference level adjacent to discrete locations on each of the one or more selected surface areas;
   determining using the processor the average of the measured heights for each of the one or more selected surface areas;
   calculating using the processor the absolute value of the height difference between the average of the measured heights and a predetermined height to generate an absolute height value for each of the one or more selected surface areas; and
   selecting a marking area on an item sized and shaped to be positionable on at least one of the plurality of tooth crowns, the marking area located on the item to correspond to one of the one or more selected surface areas having an absolute height value that meets a threshold value.

9. The method of claim 8, further comprising:
   determining using a processor a slope value for each of the one or more selected areas.

10. The method of claim 9, further comprising selecting a marking area for the item corresponding to the one or more selected surface areas having at least a smallest slope value and a smallest absolute height value.

11. A system for locating and selecting a marking position on one or more selected areas of an item, the system comprising:
   a processor configured to:
      determine that one or more selected surface areas of a representation of an item have at least a minimum surface area;
      determine a plurality of height measurements relative to a reference level and the discrete locations on each of the one or more selected surface areas;
      determine the average of the measured heights for each of the one or more selected surface areas;
      calculate the absolute value of the height difference between the average of the measured heights and a predetermined height to generate an absolute height value for each of the one or more selected surface areas;
      determine a slope value for each of the one or more selected surface areas; and
      select a marking area on a physical item that corresponds to the one or more selected surface areas having the slope value and the absolute height value less than or equal to a threshold value; and
   a marking station configured to place a mark on the physical item in the marking area selected by the processor.

12. The system of claim 11, wherein the average height of the selected area comprises the mean value of heights measured from the selected area to a reference level.

13. The system of claim 11, wherein the slope value comprises the slope of a dispersion of points projected from selected area to a reference level.

14. The system of claim 11, wherein the marking station comprises a laser.

15. The system of claim 11, wherein the marking station comprises a printer.

16. The system of claim 11, wherein the physical item comprises a prosthetic device.

17. The system of claim 11, wherein the marking area comprises the surface of a dental aligner.

18. The system of claim 11, wherein the minimum surface area comprises at least one surface area that is equal to or larger than a predetermined minimum required surface area.

19. A computer implemented method for creating a marking position on one or more selected areas of an item, the method comprising:
   generating using a processor a first data set representing a first configuration, wherein the first configuration includes a dental configuration defining at least a first and second tooth crown;
   generating using a processor a second data set representing a platform area;
   forming a structure from a combination of the first data set and the second data set having the platform area positioned on a space corresponding to an area adjacent the first and second tooth crown; and
   marking the platform area on the structure with a form of identification, wherein marking the platform area includes using a laser for marking.

20. The method of claim 19, wherein marking the platform area on the structure with a form of identification comprises using an ink printing device for marking.

21. The method of claim 19, wherein marking the platform area on the structure comprises using a label adhered to the platform area.

22. The method of claim 19, wherein the structure comprises a mold configured to produce a dental aligner.

23. The method of claim 19, wherein forming the structure from the combination of the first data set comprises:
   forming an intermediate structure using the first data set;
   forming a separate platform using the second data set; and
   adhering the separate platform to the intermediate structure.

24. The method of claim 23, wherein the intermediate structure comprises a dental aligner.

25. The method of claim 19, wherein the structure is configured to produce a product taken from the group of products consisting of prosthetic devices, hearing aids and athletic gear.

26. A computer implemented method for locating a marking position on one or more selected areas of an item, the method comprising:
   determining using a processor a list of candidate locations located on one or more selected areas of a source item;
   locating using the processor candidate marking positions on the selected areas of the source item based on prescribed geometric criteria; and
   eliminating using the processor candidate marking positions from the list of candidate locations based on the failure of the candidate marking positions to meet requirements of the prescribed geometric criteria,
   wherein locating candidate marking positions on the source item based on prescribed geometric criteria comprises using the processor for:
      determining a plurality of height measurements relative to a reference level and locations on each of one or more selected areas;
      determining the average of the measured heights for each of the one or more selected areas;
      calculating the absolute value of the height difference between the average of the measured heights and an optimum height to generate an absolute height value for each of the one or more selected areas;
      determining a slope value for each of the one or more selected areas; and
      selecting a marking area that corresponds to the candidate marking position having at least the smallest slope value and the smallest absolute height.

27. The method of claim 26, wherein determining a list of candidate locations comprises determining that the one or more selected areas of the source item has at least a minimum surface area.

* * * * *

UNITED STATES PATENT AND TRADEMARK OFFICE
CERTIFICATE OF CORRECTION

| | | |
|---|---|---|
| PATENT NO. | : 7,840,373 B2 | Page 1 of 1 |
| APPLICATION NO. | : 11/755652 | |
| DATED | : November 23, 2010 | |
| INVENTOR(S) | : James C. Culp et al. | |

It is certified that error appears in the above-identified patent and that said Letters Patent is hereby corrected as shown below:

On first page, in field (57), under "ABSTRACT", in column 2, line 2, delete "meets meet" and insert -- meets --, therefor.

In column 11, line 32, in claim 23, after "data set" insert -- and the second data set --.

Signed and Sealed this
Twenty-fifth Day of January, 2011

David J. Kappos
*Director of the United States Patent and Trademark Office*